(12) United States Patent
Hertz

(10) Patent No.: US 9,345,827 B2
(45) Date of Patent: May 24, 2016

(54) OBTAINING CONTROL SETTINGS FOR A DIALYSIS MACHINE

(75) Inventor: Thomas Hertz, Lund (SE)

(73) Assignee: Gambro Lundia AB, Lund (SE)

( * ) Notice: Subject to any disclaimer, the term of this patent is extended or adjusted under 35 U.S.C. 154(b) by 473 days.

(21) Appl. No.: 13/825,198

(22) PCT Filed: Sep. 20, 2011

(86) PCT No.: PCT/EP2011/066253
§ 371 (c)(1),
(2), (4) Date: Jun. 24, 2013

(87) PCT Pub. No.: WO2012/038384
PCT Pub. Date: Mar. 29, 2012

(65) Prior Publication Data
US 2013/0274644 A1    Oct. 17, 2013

Related U.S. Application Data

(60) Provisional application No. 61/384,341, filed on Sep. 20, 2010.

(30) Foreign Application Priority Data

Sep. 20, 2010 (SE) ...................................... 1050974

(51) Int. Cl.
*A61M 37/00* (2006.01)
*A61M 1/16* (2006.01)
(Continued)

(52) U.S. Cl.
CPC ............... *A61M 1/16* (2013.01); *A61M 1/1611* (2014.02); *A61M 1/1613* (2014.02); *A61M 1/3609* (2014.02); *G06F 19/3481* (2013.01); *A61M 2205/52* (2013.01); *G06F 19/345* (2013.01)

(58) Field of Classification Search
CPC ....... A61M 1/16; A61M 1/1601; A61M 1/14; A61M 1/34; A61M 1/36; A61M 2205/35; A61M 1/1613; A61M 1/3609; G06F 19/3418
USPC .......................................... 604/4.01–6.16, 29
See application file for complete search history.

(56) References Cited

U.S. PATENT DOCUMENTS

| 5,744,031 A | 4/1998 | Bene |
|---|---|---|
| 5,938,938 A | 8/1999 | Bosetto et al. |

(Continued)

FOREIGN PATENT DOCUMENTS

| DE | 10 2006 032 926 A1 | 1/2008 |
|---|---|---|
| EP | 1 396 274 A1 | 3/2004 |

(Continued)

*Primary Examiner* — Philip R Wiest
(74) *Attorney, Agent, or Firm* — K&L Gates LLP

(57) ABSTRACT

Prior to each treatment session for an individual patient, a machine controller in a dialysis machine obtains from a logic device a set of current control settings of the machine-related parameters to be applied in the treatment session. In generating the control settings, the logic device obtains a set of therapeutic targets comprising a target value that represents part of a desired status of the patient after the treatment session, in terms of one or more physiological parameters for the patient. The logic device also obtains status data that represents the current status of the patient prior to the treatment session, and computes the set of current control settings of the machine-related parameters, as a function of the set of therapeutic targets and the status data and at least partly based on a predictive model, which estimates the physiological response of the patient to the machine-related parameters during the treatment session.

30 Claims, 4 Drawing Sheets

(51) Int. Cl.
*A61M 1/36* (2006.01)
*G06F 19/00* (2011.01)

(56) References Cited

U.S. PATENT DOCUMENTS

| | | |
|---|---|---|
| 2001/0037968 A1 | 11/2001 | Bene et al. |
| 2004/0057037 A1 | 3/2004 | Ohishi et al. |
| 2006/0157413 A1 | 7/2006 | Bene et al. |
| 2007/0135750 A1 | 6/2007 | Kraemer |
| 2007/0175827 A1 | 8/2007 | Wariar |
| 2007/0215545 A1 | 9/2007 | Bissler et al. |
| 2009/0101550 A1* | 4/2009 | Muller et al. .................. 210/87 |
| 2010/0010424 A1 | 1/2010 | Yu et al. |
| 2010/0010428 A1 | 1/2010 | Yu et al. |
| 2010/0168925 A1 | 7/2010 | Hilgers et al. |

FOREIGN PATENT DOCUMENTS

| | | |
|---|---|---|
| EP | 1 419 794 A1 | 5/2004 |
| WO | 93/00938 A1 | 1/1993 |
| WO | 97/44072 A1 | 11/1997 |
| WO | 01/41831 A2 | 6/2001 |
| WO | 2010004400 A2 | 1/2010 |
| WO | 2010108955 A1 | 9/2010 |
| WO | 2010130449 A1 | 11/2010 |

* cited by examiner

| Parameter | Priority | Value definition |
|---|---|---|
| Duration | 1 | Fixed |
| Dialyzer | 2 | Any |
| Blood flow rate | 4 | Normal for patient |
| Dialysis fluid rate | 5 | As high as possible |
| Electrolyte 1 | 6 | Within limits |
| . | . | . |
| Electrolyte n | 6 | Within limits |
| UF rate | 3 | Achieve UFV target |

| Parameter | Priority | Value definition |
|---|---|---|
| Duration | 2 | Whatever needed |
| Dialyzer | 5 | Any |
| Blood flow rate | 4 | Within limits |
| Dialysis fluid rate | 1 | Achieve saturation |
| Electrolyte 1 | 6 | Within limits |
| . | . | . |
| Electrolyte n | 6 | Within limits |
| UF rate | 3 | Achieve UFV target |

FIG. 4B

| Parameter | Priority | Value definition |
|---|---|---|
| Duration | 1 | Fixed |
| Dialyzer | 5 | Any |
| Blood flow rate | 4 | Within limits |
| Dialysis fluid volume | 1 | Available |
| Dialysis fluid rate | 2 | Within limits |
| Electrolyte 1 | 6 | Within limits |
| . | . | . |
| Electrolyte n | 6 | Within limits |
| UF rate | 3 | Achieve UFV target |

FIG. 4C

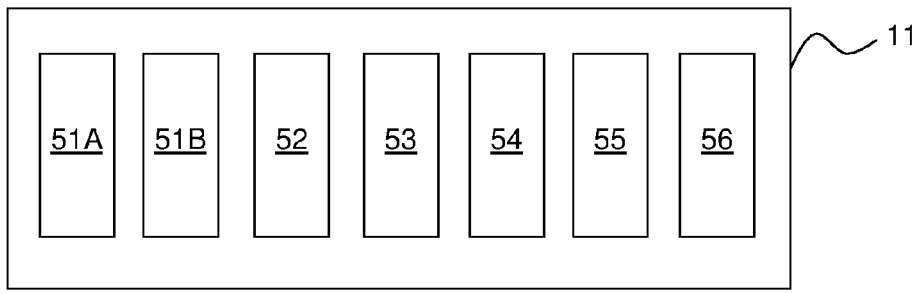

Fig. 5

OBTAINING CONTROL SETTINGS FOR A DIALYSIS MACHINE

TECHNICAL FIELD

The present invention relates to the field of renal replacement therapy by use of a dialysis machine, in particular a technique of obtaining control settings for such a dialysis machine.

BACKGROUND ART

Treatment of a patient with renal insufficiency is typically carried out according to a treatment plan created by a caregiver, such as a physician, based on certain therapeutic objectives or targets. The treatment plan may comprise a schedule of treatment sessions and specific control settings of the dialysis machine for each scheduled treatment session. The control settings are given for a number of machine-related parameters, such as duration, dialysis fluid composition, dialysis fluid flow rate, blood flow rate, type of dialyzer, etc. The control settings for each treatment session are normally strictly adhered to. The treatment plan typically also includes dietary advice, medications, frequency of blood samples for follow-up, etc.

The overall goal of the treatment plan is to achieve a desired patient status, viz. normalization of fluid balance and blood parameters of the patient. This may include normalization of fluid status, removal of uremic toxins, normalization of acid/base balance, and normalization of specific electrolytes, such as sodium, potassium, calcium, phosphate, etc. The caregiver designs the treatment plan based on clinical experience and knowledge about the specific patient. The outcome of the treatment plan may be followed by taking regular blood samples, e.g. monthly, allowing the treatment plan to be adjusted by the caregiver to better achieve the desired patient status.

This technique of determining the control settings of the dialysis machine and other aspects of the treatment plan presumes that each treatment session is scheduled according to the treatment plan and is carried out exactly with the prescribed control settings. In other words, it does not allow for any flexibility in when and how to carry out an individual treatment session. In the future, it may be foreseen that more renal replacement therapy will be carried out in the home of the patient, instead of in a clinic. In such a situation, the patient may desire to schedule the treatment sessions more according to his/her wishes and less according to a fixed schedule. It is not unlikely that increased demands for flexibility may arise also in clinical environments.

The current technique of determining the treatment plan requires involvement of the caregiver every time a change is to be made to the treatment plan. The required effort of the caregiver may also be significant, since the control settings need to be determined and re-evaluated manually, as the case may be.

Furthermore, since the treatment plan is determined empirically by the caregiver, it is not uncommon or unlikely that some patients underachieve the desired patient status and possibly develop adverse conditions.

There have been attempts in the prior art to mitigate these shortcomings.

US2010/0010424 discloses a peritoneal dialysis system that includes a number of modules which are designed to generate a number of default prescriptions to be downloaded into a dialysis machine. A prescription defines all control settings for the dialysis machine such as APD type, solution type, therapy time, and fill volume. A prescription optimization module is operated to automatically generate all possible regimens that fit within given ranges of therapy inputs, to achieve specified therapy targets for a specific patient. A filter module applies a filter that specifies the patient's preference and caregiver's performance requirement to narrow the number of regimens to a manageable few. The caregiver and patient then agree upon 3-5 regimens, which are downloaded as default prescriptions into the dialysis machine. For example, the default prescriptions may be a low UF (ultrafiltration) prescription, a standard UF prescription and a high UF prescription. At the onset of a treatment session, the machine may automatically select one of the default prescriptions, based on the patient's daily weight and possibly the patient's blood pressure. Alternatively, the machine may allow the user to choose from one or more default prescriptions.

Although this system offers increased flexibility in scheduling treatment sessions, the patient still has limited options and the treatment session may result in significant deviations from the desired patient status.

US2007/0175827 discloses a renal disease management system with a renal therapy device and an implanted cardiac rhythm management (CRM) device having sensors for measuring physiological parameters of the patient. The measured physiological parameters are transmitted to the renal therapy device which is configured to modify the renal therapy applied to the patient in response to the received parameters. Thus, the system includes feedback control that modifies the control settings of the renal therapy device during the course of a treatment session.

By the same token, EP1396274 discloses a blood treatment equipment capable of adjusting the duration of treatment session to achieve a prescribed dose target. The adjustment of duration is based on actual measurements of dialysance during treatment, and recalculation of remaining time. This system also reacts to measured changes during the course of a treatment session based on feedback control.

Neither of these systems provide any assistance for the caregiver or the patient in determining appropriate control settings for the treatment session.

The prior art also comprises WO93/00938 which discloses a control system for a dialysis unit. The control system is connected to sensors for monitoring parameter changes in plasma volume, total weight loss and total sodium removal. The control system allows the operator of the dialysis unit to enter changes in these parameters to be achieved during a treatment session, and the control system then computes appropriate machine parameters to be used by the dialysis unit. The control system is operable in an automatic control mode, in which the control system uses a mathematical model that describes the patient-dialysis unit system as an isolated system with the machine parameters as input and the changes as output. The control system is also operable in a manual mode, in which constant values of the machine parameters are calculated in a conventional way without the use of the mathematical model. Even if this system may assist the caregiver in determining control settings for a treatment session, it requires the caregiver to estimate, based on clinical experience and knowledge about the patient, the change to be achieved in each of the parameters measured by the sensors so as to attain a certain desired patient status after completion of the treatment session. This is not an easy task, and errors in the estimated changes may lead to significant deviations from the desired patient status, which ultimately may pose a risk to the patient's health.

US2004/0057037 and US2007/0135750 disclose control systems with feedback control that modifies control settings of a blood treatment device during the course of a treatment session. In US2004/0057037, the feedback control is operated to match an ideal curve for the rate of change in circulating blood volume, based on a continuous measurement of hematocrit values. In US2007/0135750, the feedback control is operated to withdraw a given amount of potassium, based on the output of a potassium-sensitive sensor in the dialysis fluid outlet line. These feedback control systems still confront the caregiver with the challenging task of estimating the changes to be achieved during the treatment, so as to attain a desired patient status.

DE102006032926 discloses a dialysis system which provides for manual input of duration and dose for a treatment session, whereupon the system calculates a desired clearance for the treatment session to achieve the dose. The desired clearance is shown to the caregiver who sets the dialysate fluid flow rate and the blood flow rate based on table data. In a variant, the dialysis system automatically determines one of the dialysate fluid flow rate and the blood flow rate, based on manual input of the other of the dialysate fluid flow rate and the blood flow rate. Although this system may offer increased flexibility in scheduling treatment sessions, the patient still has limited options since at least one of duration and clearance needs to be fixed. Furthermore, the treatment session is controlled with respect to dose (KT/V), which is a known measure of the effectiveness of a treatment, but has no causality with the physiological status of the patient after the treatment session. Thus, even if the caregiver empirically estimates a dose for the treatment session, the physiological status of the patient after the treatment session may deviate from the desired patient status.

SUMMARY

It is an object of the invention to at least partly overcome one or more of the above-identified limitations of the prior art.

Another objective is to provide a technique of controlling a dialysis machine so as to allow for greater freedom of scheduling treatment sessions.

A still further objective is to provide a technique of controlling a dialysis machine that ensures or at least improves the likelihood that an adequate patient status is achieved by the treatment.

Yet another objective is to provide a technique of controlling a dialysis machine that reduces the effort required by the caregiver.

One or more of these objects, and further objects that may appear from the description below, are at least partly achieved through a dialysis system, uses of a dialysis system, a logic device for generating control settings to a dialysis machine, a method of obtaining control settings for a dialysis machine, and a computer program product according to the independent claims, embodiments thereof being defined by the dependent claims.

A first aspect of the invention is a dialysis system. The dialysis system comprises a dialysis machine configured to perform treatment sessions of renal replacement therapy, and a logic device for generating control settings of machine-related parameters of the dialysis machine. The dialysis machine is configured to obtain from the logic device, prior to each treatment session for an individual patient, a set of current control settings of the machine-related parameters to be applied in the treatment session. The logic device is configured to: obtain a set of therapeutic targets comprising a target value of one or more physiological parameters for the patient, wherein the target value represents part of a desired status of the patient after the treatment session; obtain status data that represents a current status of the patient prior to the treatment session; and compute, as a function of the set of therapeutic targets and the status data, the set of current control settings of the machine-related parameters, wherein the logic device is configured to compute at least part of the set of current control settings based on a predictive model that estimates the physiological response of the patient to the machine-related parameters during the treatment session, such that the set of current control settings of the machine-related parameters enable the dialysis machine to achieve said target value of one or more physiological parameters for the patient at the end of the treatment session.

Under of the first aspect, the dialysis system does not require the user to choose from a limited number of predetermined default control settings. Instead, the dialysis system computes suitable control settings for each individual treatment session based on the status of the patient before the treatment session and the set of therapeutic targets given for the patient. In other words, the dialysis system is controlled towards the set of therapeutic targets for each individual treatment session. This means that the dialysis system does not have to strictly adhere to a treatment plan that stipulates the scheduling of treatment sessions and the course of each treatment session. As long as the current status of the patient prior to the treatment session is determined, estimated or otherwise provided to or by the dialysis system, the treatment sessions may be scheduled more or less according to the wishes of the patient or the caregiver, of course within overall limits to maintain the health of the patient.

Furthermore, the dialysis system of the first aspect is controlled based on a set of therapeutic targets that comprise a target value that represents part of the desired status of the patient after the treatment, in terms of one or more physiological parameters of the patient. This means that the dialysis system is explicitly operated to achieve the target value of the physiological parameter during the treatment session. In the context of the present disclosure, the term "physiological parameter" denotes any physiology-related quantity that may be monitored to determine one or more quantitative physiological levels associated with an individual. The target value may thus been seen as a measurable quantity of a physiological parameter. A collection of values of different physiological parameters may be seen to define the physiological status of the patient ("desired status"). Thus, instead of operating the dialysis system towards a treatment parameter such as dose, and then verifying the physiological status of the patient after the treatment session by means of blood samples or the like, the dialysis system is controlled towards a target value that represents part of the desired patient status after the treatment session. It should be realized that this increases the likelihood that an adequate patient status is achieved by the treatment session.

The first aspect may also reduce the effort required by the caregiver, who may define at least part of the set of therapeutic targets in terms of a target value of a physiological parameter for the patient, whereupon the logic device calculates the appropriate control settings to achieve the target value which represents part of the desired patient status. Thus, the first aspect mitigates or even eliminates the need for the caregiver to manually estimate the control settings for the treatment session, a target value of a treatment parameter such as dose, or a desired change in a physiological parameter.

The ability of the dialysis system of the first aspect to be operated towards a target value that represents part of the desired patient status is achieved by configuring the logic device to compute at least part of the current control settings based on a predictive model that estimates the physiological response of the patient to the machine-related parameters during the treatment session. The predictive model may thus be seen to link the resulting patient status to the operation of the dialysis machine, and provides a computational vehicle for the logic device to compute the control settings based on the status data and the target value of the physiological parameter(s). Different predictive models are known in the art, but have not previously been implemented for this purpose. The complexity of the predictive model may vary, e.g. depending on the physiological parameter(s) and on the required precision of the dialysis system in achieving the target value of the physiological parameter(s). The predictive model may be purely empirical, purely theoretical, or a combination thereof.

It should be noted that the dialysis system of the first aspect does not rely on feedback control, e.g. via on-line measurements of the physiological parameters, although the dialysis system may be implemented to account for such on-line measurements by calculating updated control settings (see below).

The set of therapeutic targets may be obtained by the logic unit via manual input through a user interface, such as a keyboard, touch screen, etc. Alternatively, the logic device may obtain the set of therapeutic targets from an electronic memory, which is located in the dialysis machine, on a server, on a removable storage device such as a patient specific memory device (e.g. memory card, flash card, chip card, USB memory, etc), or is otherwise accessible to the logic device.

The status data may likewise be obtained by the logic unit via manual input or from an electronic memory. Alternatively, the status data may be calculated or estimated by the logic device, as will be further explained below.

The control settings that are computed by the logic device may include a fixed value of a machine-related parameter and/or a temporal profile, i.e. a time-sequence of values of the machine-related parameter during the course of the treatment session or part thereof. The machine-related parameters may comprise at least one of a duration of the treatment session, a dialyzer type, a blood flow rate, a dialysis fluid flow rate, a dialysis fluid composition, an ultrafiltration rate, or any other relevant parameter for the operation of the dialysis machine.

In one embodiment, the logic device is configured to compute the current control settings for the machine-related parameters without user intervention. The logic device may thus automatically provide the current control settings based on the therapeutic targets and the status data.

In one embodiment, the dialysis machine is configured to perform the treatment session by use of the current control settings that are computed by the logic device.

The dialysis machine may, e.g., be configured for one of hemodialysis, hemodiafiltration, hemofiltration and peritoneal dialysis.

The logic device may be physically separate from the dialysis machine. For example, the logic device may be implemented by software run on a separate processing unit, such as a computer or a server, which is wired or wirelessly connected to the dialysis machine. Alternatively, the logic device may be physically combined with the dialysis machine. It is also conceivable that the logic device is fully or partly implemented by software run on a processor in the dialysis machine.

In one embodiment, the dialysis system is configured to, before the dialysis machine performs the treatment session, present at least part of the current control settings for approval by a user. The settings may be presented via a user interface which, depending on implementation, may be integrated with the dialysis machine or the logic device, or may be a separate component.

In one embodiment, the dialysis system is configured to, if a modification of one or more current control settings is received after presenting said at least part of the current control settings, cause the logic device to compute updated control settings based on the modification. Thereby, the patient or the caregiver is given the option of modifying the control settings as computed by the logic device. For example, the patient may desire to shorten the duration of the treatment session, or the caregiver may desire to change the blood flow rate or the dialysis fluid flow rate. In one implementation, the logic device may treat the modified control setting(s) as a fixed value when computing updated control settings. In another implementation, the logic device is configured to temporarily update the value definition (see below) with the modified control setting. Alternatively or additionally, the logic device may be configured to temporarily update the priority order (see below), e.g. by increasing the priority of the machine-related parameter that has been modified by the user. By updating at least one of the value definition and the priority order, the logic device is given more freedom to optimize the set of control settings with respect to achieving the therapeutic targets.

In one embodiment, the set of therapeutic targets represents the desired status of the patient after the treatment session. By defining the therapeutic targets in terms of the desired patient status, the task of the caregiver to set the therapeutic targets is facilitated further, and the likelihood that an adequate patient status is achieved by the treatment session is improved. For example, the set of therapeutic targets may include the target values of all physiological parameters that define the desired status. It is of course possible that the set of therapeutic targets, in addition to the target value of the physiological parameter(s), comprises other types of therapeutic targets as well, e.g. the above-mentioned dose. However, in one embodiment, the set of therapeutic targets consists of target values of a plurality of physiological parameters. Thereby, the therapeutic targets are exclusively defined by target values of physiological parameters, and the dialysis machine is controlled to achieve these target values.

In one embodiment, the set of therapeutic targets comprises target values of at least two physiological parameters. In one such embodiment, the physiological parameters comprise a measure of a property of the patient's blood, and a measure of a fluid balance of the patient. For example, target value for the fluid balance may be given as a "dry weight" of the patient, i.e. the weight of the patient after the treatment session. The property of the patient's blood may comprise at least one of a concentration of urea, a concentration of an electrolyte, and an acid-base balance. For example, the target value may represent a maximum concentration of a relevant substance in the plasma of the patient after the treatment session. The reference to "after the treatment session" as used hereinabove may refer to a time point near or at the end of the treatment session, a time point after or during a so-called rebound, or any other subsequent time point.

In one embodiment, the status data comprises a starting value of said one or more physiological parameters before the treatment session. Thereby, the status data and the therapeutic target are defined as values of one and the same parameter(s). This may facilitate the computation of the control settings.

In this context, the logic device may be configured to estimate the starting value of said one or more physiological parameters based on historic data for the patient. The historic data may be may be accessible to the logic unit via manual input, as stored on an electronic memory, or from an on-line measurement system, or a combination thereof.

In one embodiment, the historic data indicates a rate of change for at least one physiological parameter. If the rate of change is known, the starting value may be computed by extrapolation from at least one value of the physiological parameter at a known time point. The extrapolation may be linear, polynomial, or of any other suitable type. The use of historic data provides a simple way of estimating the starting value with a sufficient precision for many implementations. It is to be understood that the historic data may, but need not, comprise a rate of change value or a rate of change function. Instead, the historic data may be made up of values of the physiological parameter at different preceding time points, allowing the rate of change to be estimated and/or used in the calculation of the starting value.

In one conceivable example, physiological parameter is a measure of the amount of urea in the patient's blood, and the historic data is given as the urea generation rate between the treatment sessions. The urea generation rate is e.g. dependent on the food intake between the treatment sessions. Presuming that an actual or average urea generation rate has been estimated for the patient, the logic device may calculate a starting value for the concentration of urea in the patient's blood based on the urea generation rate and a previously known or estimated urea concentration value, e.g. taken as the target value of a preceding treatment session or a measured value at some previous time point.

It is generally conceivable that the historic data may comprise data related to one or more preceding treatment sessions, including at least one of a time between treatment sessions, a duration of one or more preceding treatment sessions, a clearance obtained in one or more preceding treatment sessions, a final value of said one or more physiological parameters in one or more preceding treatment sessions.

In one embodiment, the logic device is configured to estimate the starting value of said one or more physiological parameters by means of a further predictive model that estimates the status of the patient based on the historic data. Different types of predictive models are known in the art, but they have not been applied for generating starting values to be used for computing control settings of a dialysis machine. The complexity of the predictive model may vary, e.g. depending on the physiological parameter(s) and on the required accuracy of the starting value(s). The predictive model may be purely empirical, purely theoretical, or a combination thereof.

In one embodiment, the logic device is configured to calculate session targets as a difference between the target and starting values for each physiological parameter, and compute the current control settings as a function of the session targets. The session targets may e.g. indicate an amount of each substance to be removed or added to the patient during the treatment session. The use of these differential session targets may facilitate the calculation of current control settings. However, session targets need not be used.

In one embodiment, the logic device is configured to compute said at least part of the current control settings by finding one solution to a set of functional relations, wherein each functional relation is obtained based on the predictive model and links one of said one or more physiological parameters to one or more machine-related parameters. The set of functional relations may be seen to form a system of equations. The system of equations is typically underdetermined and thus has a large or infinite number of solutions. The logic device may be configured to select one solution arbitrarily, or locate the solution using any standard technique such as parameterization or optimization, as in known to the person skilled in the art of mathematics.

In one embodiment, the logic device is configured to find said one solution by computing the values of the machine-related parameters according to a predetermined priority order. The priority order enables the logic device to find one or a few solutions to the functional relations in a processing-efficient and flexible way. The priority order is actively used within the process of finding a suitable solution to the functional relations. The number of computation operations is significantly reduced compared to first finding all possible solutions to the functional relations and then applying a filter to select one solution.

In one embodiment, the logic device is further configured to obtain a data structure that defines the predetermined priority order. Thereby, the logic device may be tailored to many different environments, such as in-center, at home, at hospital, etc. The data structure, which may be obtained from an electronic memory on the dialysis machine or on a server, may e.g. be specified by the caregiver to fit the specific environment.

Additionally or alternatively, the logic device may be configured to find said one solution by computing the values of the machine-related parameters based on predetermined value definitions for the values of the machine-related parameters. The value definitions are thus constraints which are actively used within the process of finding a suitable solution to the functional relations. Similarly to the priority order, the logic device may be configured to obtain a data structure that contains the value definitions, e.g. from an electronic memory. The use of such a data structure enables the logic device to be tailored to many different environments. The value definitions may comprise at least one of: setting the value of at least one machine-related parameter to a predetermined value, setting the value of at least one machine-related parameter to a minimum, setting the value of at least one machine-related parameter to a maximum, and setting the value of at least one machine-related parameter to any value. Evidently, value definitions such as "minimum", "maximum" and "any" are not arbitrary, but are set within physical limits of the dialysis system to achieve the target value of the physiological parameter(s). Possibly, "minimum", "maximum" and "any" are further confined within overall limits for the dialysis machine, such as performance limits, medically safe limits, and limits set to avoid complications for the patient. These overall limits may or may not be explicitly included in the value definitions.

In a specific implementation, the value definitions indicate a dialysis fluid flow rate to be set to achieve saturation, and wherein the priority order prioritizes the dialysis fluid flow rate over a duration of the treatment session. This implementation may be advantageous if one wants to optimize the use of the available dialysis fluid, e.g. if the volume of dialysis fluid is limited.

In another specific implementation, the value definitions indicate a given amount of dialysis fluid to be utilized over the duration of the treatment session, and the priority order prioritizes the amount of dialysis fluid and the duration of the treatment session over the dialysis fluid flow rate. This implementation may be advantageous if one wants to use a given amount of dialysis fluid, e.g. the amount of dialysis fluid that is available for the upcoming treatment session, to the maximum during the treatment session, which may or may not have a fixed duration.

In another specific implementation, the value definitions indicate the duration of the treatment session to be set to a minimum, and the priority order prioritizes the duration of the treatment session over other machine-related parameters.

This implementation may be advantageous to achieve short yet effective treatment sessions.

In yet another specific implementation, the logic device is configured to set the duration of the treatment session to a predetermined value when computing the current control settings. This embodiment may e.g. be used in clinics that have fixed time slots for each treatment session.

In one embodiment, the logic device is configured to separately compute a minimum duration of the treatment session to reach the target value for each physiological parameter, and set a duration of the treatment session to the maximum of the minimum durations, wherein the logic device is configured to compute the current control settings based on the thus-set duration. This is a simple and effective algorithm for ensuring that the dialysis machine is operated to achieve the therapeutic targets with a minimum duration of the treatment session.

In one embodiment, the dialysis system is configured to, if detecting a deviating value of a physiological or machine-related parameter during the treatment session, cause the logic device to compute updated control settings based on the deviating value. The updated control settings are suitably computed in the same way as the current control settings and with the aim of achieving the therapeutic targets for treatment session. The deviating value may be caused by a user entering, via a user interface, a modified control setting or a modified value of a physiological parameter, which may or may not be included in the therapeutic targets. For example, a user may choose to change the duration of the treatment or the ultrafiltration rate. The deviating value may instead originate from an on-line measurement system capable of, e.g., measuring the clearance or the blood flow rate achieved by the dialysis system or the sodium concentration in the patient's plasma. In one implementation, the logic device may treat the deviating value as a fixed value when computing updated control settings. In another implementation, the logic device may be configured to temporarily update the value definition and/or the priority order based on the deviating value.

A second aspect of the invention is a use of the dialysis system of the first aspect for performing a treatment session.

A third aspect is a use of the dialysis system of the first aspect for performing one of hemodialysis, hemodiafiltration, hemofiltration and peritoneal dialysis.

A fourth aspect of the invention is a logic device for generating control settings to a dialysis machine which is configured to perform treatment sessions of renal replacement therapy. The logic device is adapted to generate, prior to each treatment session for an individual patient, a set of current control settings of machine-related parameters to be applied in the treatment session. The logic device comprises: means for obtaining a set of therapeutic targets comprising a target value of one or more physiological parameters for the patient, wherein the target value represents part of a desired status of the patient after the treatment session; means for obtaining status data that represents a current status of the patient prior to the treatment session; and means for computing, as a function of the set of therapeutic targets and the status data, the set of current control settings of the machine-related parameters, wherein the means for computing is configured to compute at least part of the current control settings based on a predictive model that estimates the physiological response of the patient to the machine-related parameters during the treatment session, such that the set of current control settings of the machine-related parameters enable the dialysis machine to achieve said target value of one or more physiological parameters for the patient at the end of the treatment session.

The fourth aspect shares the advantages and technical effects of the first aspect. It is also to be understood that the logic device may be configured to generate, cause or otherwise provide any of the features defined in the above-mentioned embodiments of the first aspect.

A fifth aspect of the invention is a method of obtaining control settings for a dialysis machine which is configured to perform treatment sessions of renal replacement therapy. The method comprises, prior to each treatment session for an individual patient, the steps of: obtaining a set of therapeutic targets comprising a target value of one or more physiological parameters for the patient, wherein the target value represents part of a desired status of the patient after the treatment session; obtaining status data that represents a current status of the patient prior to the treatment session; and computing, as a function of the set of therapeutic targets and the status data, a set of current control settings of machine-related parameters to be controlled during the treatment session, wherein at least part of the current control settings is computed based on a predictive model that estimates the physiological response of the patient to the machine-related parameters during the treatment session, such that the set of current control settings of the machine-related parameters enable the dialysis machine to achieve said target value of one or more physiological parameters for the patient at the end of the treatment session.

The fifth aspect shares the advantages and technical effects of the first aspect. It is also to be understood that the method of obtaining control settings may involve using, obtaining, causing or otherwise providing any of the features defined in the above-mentioned embodiments of the first aspect.

A sixth aspect of the invention is a computer program product comprising computer code which, when executed on a data-processing system, is adapted to carry out the method of the fifth aspect.

Still other objectives, features, aspects and advantages of the present invention will appear from the following detailed description, from the attached claims as well as from the drawings.

BRIEF DESCRIPTION OF DRAWINGS

Embodiments of the invention will now be described in more detail with reference to the accompanying schematic drawings.

FIG. 3 is a flow chart of an embodiment of the step of computing control settings included in the method of FIG. 2.

FIGS. 4A-4C are examples of optimization data provided to the logic device in the dialysis system of FIG. 1 for use when computing the control settings.

FIG. 5 is a block diagram of a logic device for use in the method in FIG. 2.

DETAILED DESCRIPTION OF EXAMPLE EMBODIMENTS

Figure 1:
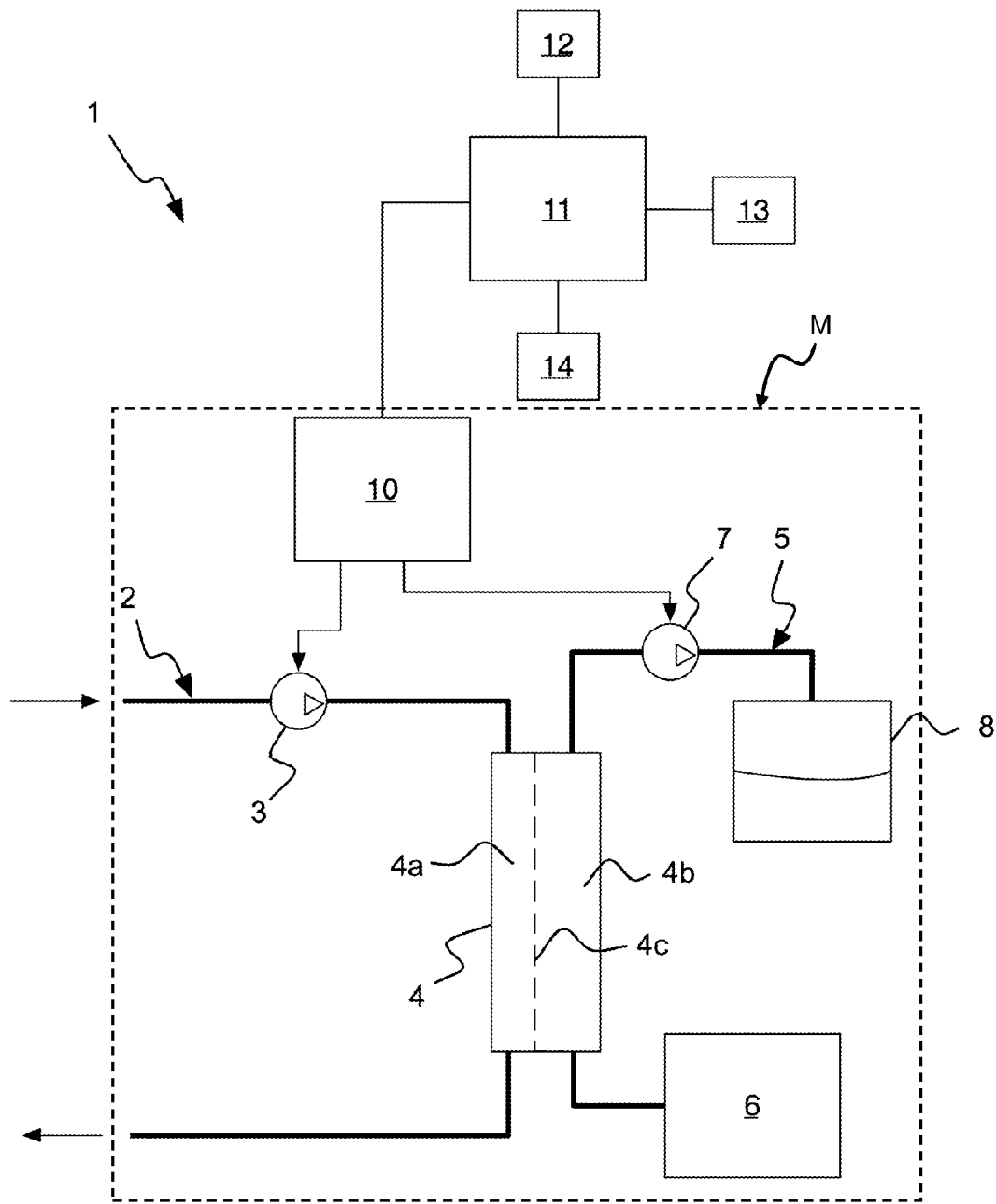
FIG. 1 is a diagram of a dialysis system that includes a logic device for providing control settings for operating the dialysis system.

In the following, for the purpose of illustration only, embodiments of the invention will be described in the context of a dialysis system for performing hemodialysis treatment. Throughout the description, the same reference numerals are used to identify corresponding elements.

FIG. 1 is a schematic view of a dialysis system 1 for hemodialysis treatment. The system defines an extracorporeal blood path 2, which extends from an access device (not shown) for blood extraction from a human or animal subject, via a blood pump 3, through a filtration unit 4 and back to an access device (not shown) for blood reintroduction into the subject. In operation, the blood pump 3 forces blood from the subject through the filtration unit 4 and back to the subject. The filtration unit 4 may be any type of blood filter device (also denoted "dialyzer") suitable for ultrafiltration and diffusive exchange, such as a coil dialyzer, a parallel plate dialyzer, a hollow fiber dialyzer, etc. The filtration unit 4 generally has a blood side 4a and a dialysis fluid side 4b separated by a semipermeable membrane 4c.

The system 1 also defines a dialysis fluid path 5 that extends from a source 6 of dialysis fluid, through the filtration unit 4 via a dialysate fluid pump 7 to a receiving unit 8 of spent dialysis fluid, e.g. in the form of a collection vessel or a drain. In operation, the dialysis fluid pump 7 forces dialysis fluid from the source 6 through the filtration unit 4 to the receiving unit 8. The source 6 of dialysis fluid may be in the form of one of more containers of pre-manufactured solutions, or it may be a system for on-line preparation of dialysis fluid.

Although not shown on the drawing, it is to be understood that the dialysis system 1 typically includes several additional components, such as a deaeration chamber, further fluid pumps, pressure sensors, conductivity sensors, an air detector, a blood leak detector, etc. It is also possible that one or more components of the dialysis machine M in FIG. 1 are not part of the dialysis machine, but are configured as a separate device, e.g. the source 6 and the receiving unit 8.

Hemodialysis is a technique for removing waste products such as creatinine and urea, as well as free water from the blood when the kidneys are in renal failure. The principle of hemodialysis is the same as other methods of dialysis; it involves diffusion of solutes across the semipermeable membrane 4c of the filtration unit 4. Fluid removal (ultrafiltration) is achieved by altering the hydrostatic pressure on the dialysis fluid side 4c of the filtration unit 4, causing free water and some dissolved solutes to move across the semipermeable membrane 4c along a created pressure gradient. The dialysis fluid is a purified aqueous solution of mineral ions (electrolytes). Urea and other waste products, potassium, and phosphate diffuse from the blood into the dialysis fluid. The concentrations of sodium and chloride in the dialysis fluid are typically held similar to those of normal plasma to limit diffusion. The concentration of sodium bicarbonate is generally set higher in the dialysis fluid than in the blood plasma to correct blood acidity. A small amount of glucose is also commonly included in the dialysis fluid.

The dialysis system 1 also includes a machine controller 10, which is configured to control the dialysis process by means of one or more operational components, such as the blood pump 3, the dialysis fluid pump 7, the system 6 for preparation of dialysis fluid, etc. The machine controller 10 operates on control settings which are provided by a logic device 11. The machine controller 10 is also configured to respond to inputs from various sensors, such as the abovementioned pressure sensors. The machine controller 10 typically also implements one or more safety functions that detect system malfunction or hazardous situations and take appropriate action.

A subject suffering from renal insufficiency or renal failure is treated with the aim of normalizing the fluid balance and blood parameters of the subject. The subject (patient) is treated in a number of treatment sessions separated over time, where each treatment session involves circulating blood from the subject through the dialysis system 1.

According to various embodiments of the invention, the logic device 11 is configured to compute the control settings for the machine controller 10 prior to each treatment session. In the illustrated embodiment, the logic device 11 is connected to a display unit 12, a manual input unit 13, and an electronic memory unit 14. The display unit 12 may include any type of screen operable to display visual data to an operator. The manual input unit 13 may be any type of equipment that allows the operator to manually enter data into the system 1. The manual input unit 13 may include a keyboard, a mouse, a touch screen, a bar code reader, etc. The display unit 12 and the manual input unit 13 thus define a user interface. The memory unit 14 may include any type of electronic memory enabling retrieval and possibly storage of data.

In practice, the dialysis system 1 in FIG. 1 may be embodied in many different ways.

In one embodiment, the logic device 11 is implemented on a separate processing device, such as a personal computer, whereas the machine controller 10, the pumps 3, 7, the filtration unit 4, the source 6 of dialysis fluid, etc are included in a conventional dialysis machine M, as indicated by dashed lines in FIG. 1. The computer may be located next to the dialysis machine M allowing an operator to interact with the logic device 11.

In another embodiment, the logic device 11 is implemented on a remote server, which is connected for communication with the dialysis machine M. To the extent that the logic device 11 communicates with the operator of the dialysis machine M, this may be done via a user interface on the dialysis machine M. The memory unit 14 may or may not be part of the dialysis machine or the server.

In yet another embodiment, the logic device 11 is physically integrated with the dialysis machine M. For example, the logic device 11 may be implemented by software run on a processor in the dialysis machine M, e.g. in the machine controller 10. It should be realized that dedicated components for the logic device 11, such as electronic memory and a processor, may be added to the dialysis machine M to enable the integration of the logic device 11.

In either embodiment, the logic device 11 may be configured to serve the control settings to the machine controller 10, either upon request by the machine controller 10 (pull) or initiated by the logic device 11 (push).

Figure 2:
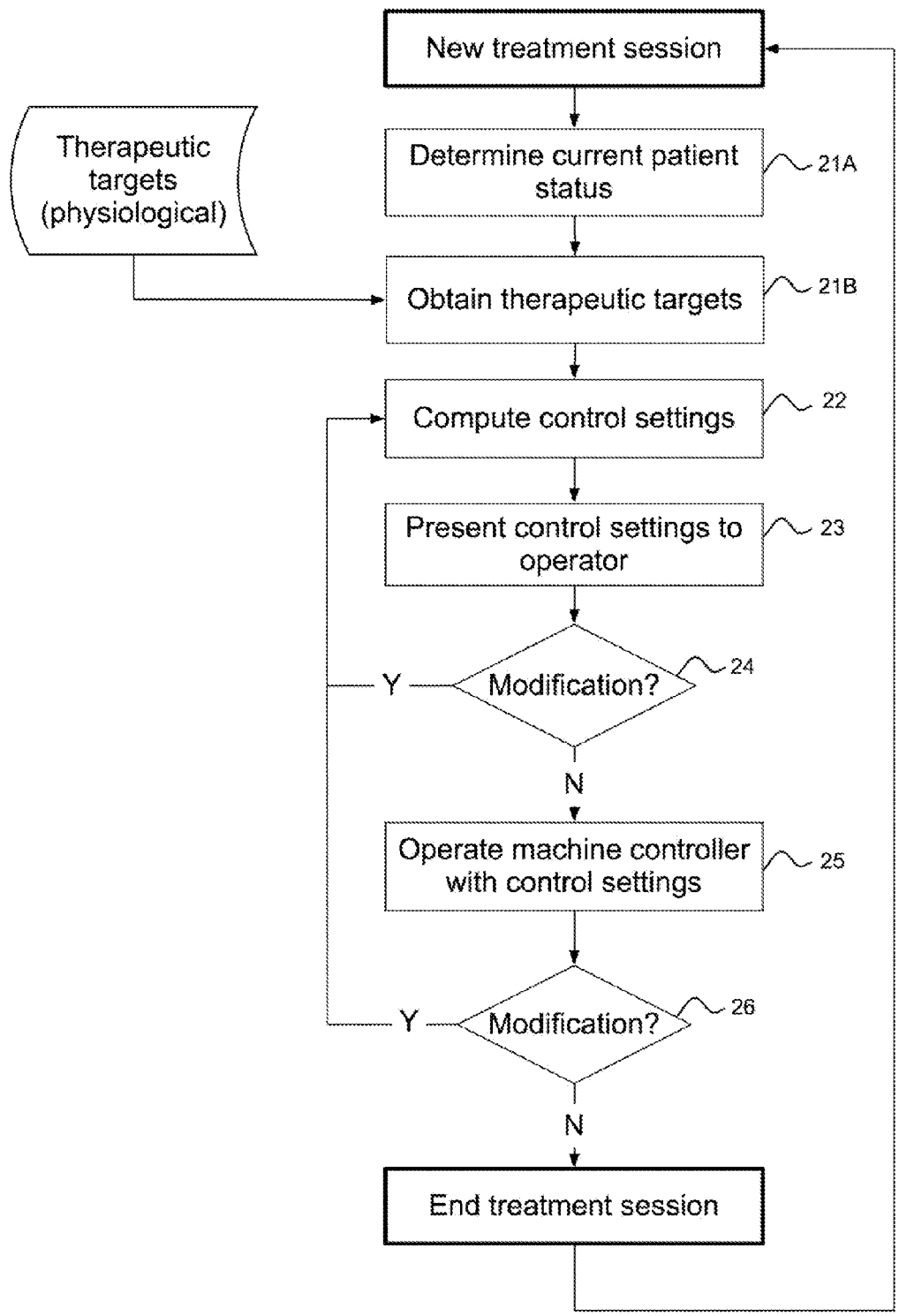
FIG. 2 is a flow chart of an method of operating the dialysis system in FIG. 1.

FIG. 2 is a flow chart of an embodiment of an overall method for operating the dialysis system 1. The individual steps shown in FIG. 2 will be exemplified in further detail in separate chapters below. The method in FIG. 2 presumes that a caregiver, such as a physician, has set therapeutic targets for the specific patient. The targets are determined once and remain unchanged unless clinical indications necessitate reconsideration. The therapeutic targets are then stored to be accessible as input data to the process of computing control settings for the machine controller 10. As will be exemplified in the following description, the therapeutic targets include values of physiological parameters of the patient to be attained at the end of the treatment session. Such a physiological parameter may be, e.g., a "dry weight", or a post-dialysis plasma concentration of urea, sodium, potassium, calcium, phosphate or bicarbonate.

A treatment session may involve the sequence of steps 21-26 shown in FIG. 2. When it is detected that a new treatment session is to be initiated, the current status of the patient is determined (step 21A). The status may be represented by current values of the physiological parameters specified by the therapeutic targets. The status may be determined by measurements of the relevant physiological parameters, or by estimation based on historic data for the patient, or a combination thereof. For example, the current weight of the patient may be (automatically or manually) obtained from a scale, while other physiological parameters may be estimated automatically, e.g. by using a predictive model of the patient. The historic data and/or patient-specific parameters for the predictive model may be retrieved from the memory unit 14 based on a unique patient identifier.

In step 21B, the therapeutic targets for the relevant patient is obtained, e.g. retrieved from the memory unit 14 based on the unique patient identifier. Then, in step 22, using the current status and the therapeutic targets, the control settings for the machine controller 10 are computed. The control settings are given in the form of values of machine-related parameters, which are parameters that represent the characteristics of the extracorporeal blood path 2, the dialysis fluid path 5 and the filtration unit 4. The control settings may stipulate either a fixed value of a machine-related parameter or a desired variation of the machine-related parameter during the session.

Step 22 is thus focused on determining suitable control settings that are deemed to result in the therapeutic targets at the end of the treatment session. Since there normally exist a multitude of combinations of values of the machine-related parameters that will achieve the targets, some parameters may be given predetermined values or value ranges (constraints) to serve as a starting point and thereby limit the alternatives. These may for example be blood flow rate and dialyzer type. The alternatives may also be limited by defining a priority order among the machine-related parameters. Step 22 is normally configured to automatically compute a single set of the control settings for the machine controller 10.

In step 23, the control settings are presented to the user, via the display unit 12, giving the operator the option to accept the control settings or to modify one or more control settings, via the manual input unit 13. It is conceivable that only a subset of the control settings are displayed or made available for modification by the operator. It is also conceivable that a modification of a control setting is only allowed within a confined range of values. If a modification is made (step 24), the process returns to step 23 to re-compute control settings based on the modified control setting(s).

In step 25, the control settings are received and used by the machine controller 10 to perform the treatment session. If a modification to a control setting or a physiological parameter is detected (step 25) during the session, the process returns to step 22 to re-compute the control settings based on the modified data. The modification may be caused by the operator changing a control setting, via the manual input unit 13, or by a change in any relevant parameter being detected by the machine controller/logic device, e.g. based on the output from a sensor/measurement system (not shown) in the dialysis system 1.

After the completion of the session, the dialysis system 1 is operable to initiate a new treatment session, for the same or a different patient.

From the operator's perspective, be it a patient or a professional caregiver, the dialysis system is very easy to configure for a treatment session. The operator simply identifies the patient to the system, and possibly enters one or more values of physiological parameters, and then the system will be set to run so as to achieve the therapeutic targets that are defined by the physician for this specific patient. The dialysis system is flexible for the operator, since it will automatically adapt the control settings in view of the current status of the patient. Thus, the sessions may be scheduled according to the wishes of the operator, while guaranteeing that the patient reaches the therapeutic targets. From the physician's point of view, the determination of suitable therapeutic targets is facilitated since these now are at least partly defined in terms of physiological parameters of the patient.

It should be emphasized that the method in FIG. 2 is merely given as an example, and that, e.g., the order of steps may be changed, and certain steps may be omitted while others may be added. For example, the dialysis system may be operated without allowing for modifications before (step 24) or during (step 26) the treatment session, or without presenting the control settings to the operator (step 23).

In the following, the steps of the method in FIG. 2 will be exemplified in greater detail. The examples will focus on the preparatory determination of therapeutic targets, the determination of the patient status (step 21A), the computation of control settings (step 22), the handling of modifications (steps 24 and 26). It may be noted that the computation of control settings is separated into a sub-step of calculating difference values, denoted "session targets", and a sub-step of computing control settings based on the session targets.

1. Setting Therapeutic Targets

The therapeutic targets are set by the physician caring for the patient. The targets are typically numbers on physiological parameters, e.g. various physical and chemical parameters of the patient, where the set numbers would be "normal" for the patient if he/she had not had the renal disease. The intention is thus that the dialysis treatment shall "normalize" the patient to the best possible extent.

The therapeutic targets are normally to be achieved after a treatment session, which may or may not be after the so-called re-bound at the end of the session. In one example, the therapeutic targets include the following physiological targets T1-T4.

T1—Normal Fluid Balance of the Patient

Specifically, this target may be given as the "dry weight" ($W_{dry}$), i.e., the target weight of the patient after fluid has been removed during a treatment session.

T2—Removal of Uremic Toxins

There are a multitude of uremic toxins of varying molecular weight generated by the body that has to be removed by dialysis. Normally, urea and creatinine are used as markers for other substances of relatively small molecular weight. For middle molecular weight vitamin B12 and for large molecules β-2-microglobuline may be used. In clinical practice today, urea is normally used as the only marker for removal of uremic toxins. Thus, this target may be set as a specific maximum concentration of urea in the plasma after a session ($C_{tt,urea}$), and may be given as mg/L or mmol/L.

T3—Normalization of Electrolytes

The electrolytes of most interest today are sodium (Na), potassium (K), calcium (Ca) and phosphate ($PO_4$). For each of these electrolytes, the therapeutic target may be set as a concentration in the plasma after the session ($C_{tt,Na}$, $C_{tt,K}$, $C_{tt,Ca}$, $C_{tt,PO4}$), and may be given as mg/L or mmol/L.

T4—Normalization of the Acid-Base Balance

Bicarbonate ($HCO_3$) is the main substance which may be controlled by dialysis and which is involved in the delicate acid-base balance in the body of the patient. Typically, bicarbonate has to be added to the patient during dialysis. The therapeutic target may be set as a concentration in the plasma after the session ($C_{tt,HCO3}$), and may be given as mg/L or mmol/L.

2. Pre-dialysis Patient Status (Step 21A)

Before each individual treatment session, the status of the patient is determined. This means measuring or estimating the pre-dialysis (starting) value of each of the physiological parameters that have been set as therapeutic targets, in this example:

The pre-dialysis weight ($W_{pre}$)

The pre-dialysis plasma urea concentration ($C_{pre,urea}$)

The pre-dialysis plasma electrolyte concentrations ($C_{pre,Na}$, $C_{pre,K}$, $C_{pre,Ca}$, $C_{pre,PO4}$)

The pre-dialysis plasma bicarbonate concentration ($C_{pre,HCO3}$)

The pre-dialysis weight ($W_{pre}$) is measured as customary by a scale.

The other pre-dialysis parameters are concentrations of substances in blood plasma. The most direct way to determine these is naturally to take a blood sample and analyze it. This will provide direct measurements of all the concentrations.

However, taking pre-dialysis blood samples before every session is impractical. It requires direct access to a blood analyzer, which most clinics do not have and almost no home patient has. An alternative method would be to use a predictive model of the water and electrolyte state of the patient's body and estimate the pre-dialysis concentrations instead.

Such predictive models have been developed and validated previously, e.g. as described in "Development and critical evaluation of an improved comprehensive multicompartment model for the exchange processes during hemodialysis", by Scharfetter et al, published in Biomed. Technik 40 (1995), pp 54-63, and "Simulation study of the intercompartmental fluid shifts during hemodialysis", by Akcahuseyin et al, published in ASAIO Journal 2000, 46:81-94. These models use multiple compartments to describe how water, electrolytes, etc are distributed in the body and how these shift between compartments. Further, the models include the dialyzer and therefore the exchange processes during dialysis may be fully simulated. The models may include any intake of substances into the body, such as the food the patient eats, which may be modeled as a constant intake of relevant substances per time unit. For further details, reference is made to the above articles and citations therein.

These types of advanced predictive models may be used to estimate the plasma concentration or the total mass of any of the substances of interest at a specific point in time. The input for such estimations may be any actual measurement of a substance, e.g. a blood sample, and the treatment history since the blood sample. The treatment history may include data on when the individual treatment sessions have been conducted, the duration and the clearance obtained during the session. Of particular interest is the time since last session, since it is during this time that most changes from the therapeutic target values have occurred.

However, it is also possible to use significantly simpler predictive models. For example, it is possible to base the estimation on previous physiological targets, i.e. the value of each physiological parameter deemed to be achieved at the end of a preceding treatment session together with the generation rate of substances for the time between the sessions.

Irrespective of estimation technique, the pre-dialysis status of the patient is represented by values of the physiological parameters $W_{pre}$, $C_{pre,urea}$, $C_{pre,Na}$, $C_{pre,K}$, $C_{pre,Ca}$, $C_{pre,PO4}$, and $C_{pre,HCO3}$ in this example.

3. Calculation of Session Targets (Step 22)

The basic intention is that each individual treatment session shall "normalize" the patient, i.e., reach the therapeutic targets. Thus, the difference between the therapeutic targets and the pre-dialysis status dictates what has to be achieved in the upcoming treatment session.

Session targets may be in the form of a specified mass of each substance that shall be removed or added to the patient.

The session target for fluid (or weight) removal ($W_{st}$) is obtained as follows:

$$W_{st} = W_{pre} - W_{dry}. \qquad (1)$$

In dialysis practice, this is sometimes known as ultrafiltration volume (UFV).

The session target for removal of uremic toxins, as represented by urea, is obtained by a series of calculations. One calculation aims at estimating the total amount of urea in the body for the "normalized" state ($M_{tt,urea}$), for the plasma urea concentration ($C_{tt,urea}$) set as therapeutic target. Such an estimation may be done with a predictive model of the type discussed above, using the physiological target $C_{tt,urea}$ as input. Another calculation aims at estimating the total amount of urea in the body in the pre-dialysis state ($M_{pre,urea}$), i.e., for the pre-dialysis plasma urea concentration ($C_{pre,urea}$). Such an estimation may be done with a predictive model of the type discussed above, using the previously measured or estimated $C_{pre,urea}$ as input. Finally, the amount of urea to be removed from the body during the treatment session is calculated according to $$M_{st,urea} = M_{pre,urea} - M_{tt,urea}. \qquad (2)$$

The session targets for the other substances of interest, i.e. the electrolytes, may be calculated in the same way. The total amount of a substance in the body is estimated for the therapeutic target and the pre-dialysis state using the predictive model, and then the amount to be removed or added during the session is calculated:

$$M_{st,Na} = M_{pre,Na} - M_{tt,Na} \qquad (3)$$

$$M_{st,K} = M_{pre,K} - M_{tt,K} \qquad (4)$$

$$M_{st,Ca} = M_{pre,Ca} - M_{tt,Ca} \qquad (5)$$

$$M_{st,PO4} = M_{pre,PO4} - M_{tt,PO4} \qquad (6)$$

$$M_{st,HCO3} = M_{pre,HCO3} - M_{tt,HCO3} \qquad (7)$$

All of these calculations may be done either as gram or as mmol. It should noted that the calculated amount may be negative, which means that the substance shall be added to, instead of removed from, the body during the treatment session (e.g. bicarbonate).

4. Determination of Control Settings Based on Session Targets (Step 22)

Once session targets have been calculated, the process may proceed determine a set of control settings for the machine controller so as to reach the session targets during the treatment session.

For a hemodialysis machine, the control settings may include values of the following machine-related parameters:

Session duration T

Dialyzer type, where the key parameter is the clearance performance that may be achieved with the selected dialyzer. This data is provided by the manufacturer, see e.g. Table 1 below. It should at this point be noted that this is a function of both blood flow rate and dialysis fluid flow rate.

Blood flow rate $Q_B$

Dialysis fluid flow rate $Q_D$

Dialysis fluid composition

Sodium concentration $C_{D,Na}$

Potassium concentration $C_{D,K}$

Calcium concentration $C_{D,Ca}$

Bicarbonate concentration $C_{D,HCO3}$
(Phosphate is normally not present in the dialysis fluid)
Ultrafiltration rate $Q_{UF}$ There are several other machine-related parameters that may be included in the method if deemed relevant for the selected therapeutic targets.

TABLE 1

In vitro clearance performance in ml/min of Gambro Polyflux Revaclear dialyzer for two dialysis fluid flow rates $Q_D$ and four blood flow rates $Q_B$ (ultrafiltration rate = 0)

| | $Q_D$ = 500 ml/min | | | | $Q_D$ = 800 ml/min | | | |
|---|---|---|---|---|---|---|---|---|
| $Q_B$ (ml/min) | 200 | 300 | 400 | 500 | 200 | 300 | 400 | 500 |
| Urea | 196 | 271 | 321 | 353 | 199 | 286 | 355 | 408 |
| Creatinine | 189 | 250 | 289 | 316 | 194 | 269 | 324 | 364 |
| Phosphate | 185 | 239 | 274 | 298 | 191 | 259 | 307 | 343 |
| Vitamin B12 | 144 | 170 | 186 | 197 | 154 | 187 | 208 | 223 |

Each of the machine-related parameters has overall limits within which it can be set. The overall limits may be given by performance limits, medical safety limits and complication-related limits.

The performance limits relate to the operation of the dialysis system. For example, the maximum dialysis fluid flow rate is typically limited by the dialysis machine. Further, the dialysis fluid flow rate may be limited by the available volume of dialysis fluid in combination with the set session duration.

The medical safety limits relate to the safety of the patient. For example, if osmotic components in the dialysis fluid (primarily sodium) fall below a certain limit, hemolysis may occur.

The complication-related limits are typically set by the physician to avoid complications for the patient. For example, the ultrafiltration rate may be limited to 800 ml/hour ($Q_{UFmax}$) to avoid hypotension, a complication partly caused by too rapid fluid volume reduction.

Since there normally exists a multitude of combinations of control settings that will achieve the therapeutic targets, some machine-related parameters have predetermined values to serve as a starting point and thereby limit the alternatives. These may include blood flow rate and dialyzer type. The blood flow rate is typically set as high as normally achievable for the specific patient and his/hers vascular access. The dialyzer type is set for practical reasons; the clinic may only have one type, or the dialysis machine may already have a dialyzer primed and ready when the patient arrives in the clinic, thus making it impractical and expensive to select another type. Alternatively, the system may be configured to request the user to identify the dialyzer of the dialysis machine, e.g. via manual input or by scanning a bar code, whereupon the control settings are computed for the thus-identified dialyzer.

Figures 3, 4A:
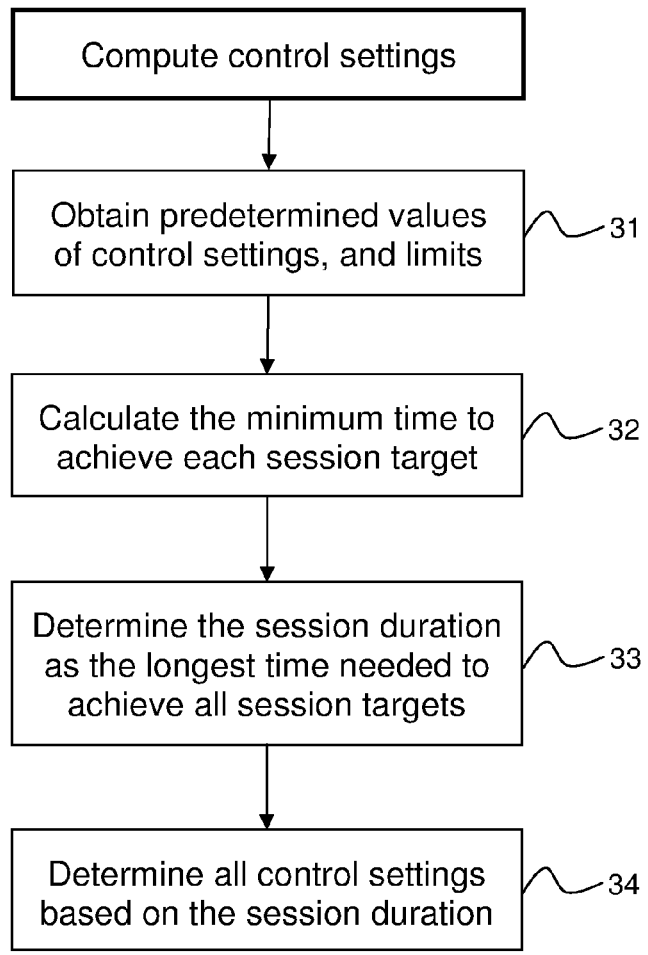

Often, the session duration T is the most important setting parameter for a user. FIG. 3 illustrates an embodiment of the step 22 of determining control settings, while optimizing the session duration. The illustrated embodiment includes a calculation process that involves a sequence of steps 31-34 which first calculates the session duration, and then adjusts other machine-related parameters accordingly.

In step 31, the process obtains the predetermined values of the machine-related parameters and the above-mentioned overall limits.

In step 32, the process calculates, for each session target, the minimum time required to achieve the session target while observing the predetermined values and the overall limits.

The minimum time to achieve the fluid removal target $W_{st}$ is $$T_{min,Wst} = \frac{W_{st}}{Q_{UF_{max}}}. \tag{8}$$

It may be more complex to calculate the minimum time $T_{min,urea}$ to achieve the uremic toxin removal target. The mass transfer rate of urea from the blood to the dialysis fluid depends on the properties of the dialyzer, the concentration $C_{urea}$ of urea in the plasma, the blood flow rate and the dialysis fluid flow rate. The properties of the dialyzer, the blood flow rate and the dialysis fluid flow rate may collectively be noted as "clearance" $K_{urea}$ (see Table 1 above). The total mass of urea removed may then be calculated by $$M_{urea}(T_x) = \int_0^{T_x} K_{urea} C_{urea}(t) dt. \tag{9}$$

It should here be noted that the clearance $K_{urea}$ depends on several factors, most notably the blood flow rate and the dialysis fluid flow rate. Data on the clearance may be obtained by the logic device from a database (e.g. stored in the memory unit 14) for each dialyzer type. To find the minimum time to achieve the uremic toxin removal target $T_{min,urea}$, the clearance is assumed to be as high as possible. Thus, the maximum achievable blood flow rate and the maximum dialysis fluid flow rate are assumed. The plasma concentration of urea $C_{urea}$ during the session is estimated using a predictive model, as exemplified above. Then, $T_{min,urea}$ is found by solving Eq. 10, where the session target $M_{st,urea}$ is met:

$$M_{st,urea} = M_{urea}(T_{min,urea}) = \int_0^{T_{min,urea}} K_{urea} C_{urea}(t) dt \tag{10}$$

Following the same procedure, the minimum times to achieve each electrolyte and acid-base normalization targets are calculated. In some of these cases, electrolytes are also present in the dialysis fluid, e.g. sodium and bicarbonate. In these cases, the concentration difference between the dialysis fluid and the plasma may need to be used instead of only plasma concentration. Using sodium as example:

$$M_{st,Na} = M_{Na}(T_{min,Na}) = \int_0^{T_{min,Na}} K_{Na}(C_{Na}(t) - C_{D,Na}) dt \tag{11}$$

As above, the minimum time is found by assuming as high a clearance as possible and as large a concentration difference as possible (within the overall limits discussed above). In this example, the dialysis fluid sodium concentration has been set to a constant value throughout the treatment session. This is in principle not required, since the process may be used for any pre-programmed concentration function (sometimes known as "profiling").

In step 33, the session duration T is calculated as:

$$T = \max(T_{min,W}; T_{min,urea}; T_{min,Na}; T_{min,K}; T_{min,Ca}; T_{min,PO4}; T_{min,HCO3}) \tag{12}$$

which represents the shortest time required to achieve all the session targets.

In step 34, the session duration T is considered fixed and the session settings are calculated to achieve the session targets in this time. In this example:

Dialyzer type is considered predetermined, and is thus not changed.

Blood flow rate $Q_B$ is considered predetermined, and is thus not changed.

Dialysis fluid flow rate $Q_D$ is given by the clearance required of the session target that determined the session duration, i.e. the substance requiring the highest clearance to reach the session target. In most cases, the flow rate $Q_D$ will be set to the maximum, although the practical limitation of availability of dialysis fluid may limit the flow rate $Q_D$.

Regarding the dialysis fluid composition, the concentration of each electrolyte is found by solving Eq. 11 for the fluid concentration with the session duration fixed. Again using sodium as an example, Eq. 11 is solved to find $C_{D,Na}$:

$$M_{st,Na} = M_{Na}(T) = \int_0^T K_{Na}(C_{Na}(t) - C_{D,Na}) dt \quad (13)$$

The other electrolyte concentrations are found in the same way.

The ultrafiltration rate $Q_{UF}$ is calculated as $$Q_{UF} = \frac{W_{st}}{T}. \quad (14)$$

In the foregoing example, two machine-related parameters (dialyzer type and achievable blood flow rate) were treated as fixed starting points, and one machine-related parameter (session duration) was prioritized in the calculation of control settings. Neither of these assumptions is necessary. In a more general embodiment, optimization data is established and made available to the logic device for use when determining the control settings. The purpose of the optimization data is to enable the logic device to calculate appropriate control settings in many different environments, such as in-center, self-care and home. The physician and/or the clinic typically determine the optimization data suitable for the specific environment.

In one embodiment, all the machine-related parameters are included in the optimization data. The optimization data may comprise two different data sets: a priority order, and value definitions. The priority order is used by the logic device to prioritize in which order the machine-related parameters shall be set, while achieving the session targets. The value definitions are constraints used by the logic device to identify the available range of values for the machine-related parameters.

Referring to the above example of a hemodialysis system, the optimization data may include: session duration T, dialyzer type (e.g. optionally specified as membrane properties and area), blood flow rate $Q_B$, dialysis fluid flow rate $Q_D$, sodium concentration $C_{D,Na}$, potassium concentration $C_{D,K}$, calcium concentration $C_{D,Ca}$, bicarbonate concentration $C_{D,HCO3}$, and ultrafiltration rate $Q_{UF}$. The value definition for session duration T may, e.g., be "as short time as possible", "always a fixed time" or "whatever time needed". The value definition for dialyzer type may, e.g., be "fixed type", "type entered by operator for session" or "any among a given set". The value definition for blood flow rate $Q_B$ may, e.g., be "fixed at normally achieved flow rate", "as high as possible", "as low as possible" or "within overall limits". The value definition for dialysis fluid flow rate $Q_D$ may, e.g., be "as high as possible", "as low as possible", "maximum saturation" or "make full use of all available fluid". The value definitions for the electrolytes may, e.g., be "within overall limits". The value definition for the ultrafiltration rate $Q_{UF}$ may e.g. by "achieve fluid removal target", "as much as possible for a given duration" or "any".

FIG. 4A illustrates an example of optimization data for use in clinics with fixed time slots for each patient. In this example, duration is prioritized over other parameters.

FIG. 4B illustrates an example of optimization data for use when the volume of available dialysis fluid is limited, i.e. when there is a desire to optimize the use or effect of the dialysis fluid. In this example, to maximize the effect of the dialysis fluid, the dialysis fluid flow rate is set to achieve saturation in the dialyzer, and dialysis fluid flow rate is prioritized over duration (and other parameters). Saturation may be achieved by setting the blood flow rate to about four times the dialysis fluid flow rate.

FIG. 4C illustrates an example of optimization data for use when there is a desire to ensure that the available dialysis fluid volume is used up during the treatment session. In this example, dialysis fluid volume is added as a machine-related parameter in the optimization data. The dialysis fluid volume is set to be equal to the available dialysis fluid volume, which may be predetermined, entered by the operator, or otherwise made accessible to the dialysis system. The optimization data prioritizes the amount of dialysis fluid and duration over dialysis fluid flow rate (and other parameters).

In FIGS. 4A-4C, the priority is indicated by numbers, with increasing number indicating decreasing priority. The priority may instead be implicit, i.e. given by the ordering of parameters.

5. Handling of Modifications (Steps 24 and 26)

Below, a few examples of different modifications that may cause the dialysis system to re-compute the control settings, either before (step 24) or during (step 26) the operation of the machine controller.

In a first example of step 24, the operator may choose to choose a shorter session duration than the one suggested by the system. This may make the system unable to reach the session targets based on the suggested control settings. The process may therefore re-compute the control settings with the updated session duration, which may result in the logic device suggesting control settings with an increased blood flow rate and/or suggesting to use a dialyzer with higher clearance.

In a second example of step 24, the operator may choose to change the control settings (e.g. by increasing session duration, blood flow rate, and/or dialysis fluid flow rate) such that the urea clearance is more than needed for reaching the session targets. This may make the system unable to meet the session targets for electrolytes. The process may therefore re-compute the control settings.

In a first example of step 26, the system or the operator may determine at the beginning of the treatment session that the blood flow rate does not reach its set value. Thereby, the clearance in the dialyzer may not be sufficient for the session targets to be reached based on the suggested control settings. The control settings may be re-computed, using the actually achieved blood flow rate as a fixed parameter value. This may result in an increase of the session duration, which is suggested to the user.

In a second example of step 26, the dialysis system may be equipped with on-line clearance monitoring technology. If it is found during the treatment session that the clearance is less than expected, the control settings may be re-computed to achieve the session targets. The expected clearance is normally the clearance value used in the computation of the original control settings (cf. Table 1 and Eq. 9-11 and 13).

In a third example of step 26, the system may determine that the plasma sodium concentration initially deviates from what is predicted by the predictive model, i.e. that the pre-dialysis concentration ($C_{pre,Na}$) was incorrectly estimated. The control settings may be re-computed based on the measured pre-dialysis concentration ($C_{pre,Na}$). The plasma sodium concentration may be given by the plasma conductivity, which in turn may be estimated by use of online clearance monitoring technology.

In a fourth example of step 26, the system may determine that the plasma sodium concentration deviates from what is expected during the treatment session, i.e. the system determines that the sodium session target cannot be reached. This may cause the system to re-compute the control settings with an increased priority for meeting the sodium session target.

In a fifth example of step 26, the patient may experience hypotensive episodes during treatment, causing the operator to manually reduce the ultrafiltration rate via the user interface. This may cause the system to re-compute the control settings, which may lead to an increase of the session duration so as to meet the session target for fluid removal (UFV).

It is not practical to re-compute the control settings for every small modification or deviation that is made or detected. Instead, a predetermined re-computation limit may be used to decide if a re-computation is to be made. The re-computation limit may be given in absolute or relative units. Depending on implementation, the modification/deviation in a machine-related parameter may be directly compared to a corresponding re-computation limit. In one example, the re-computation limit is ±10% of the expected value for each machine-related parameter used in the computation of the control settings. For example, if the blood flow rate is found to deviate more than 10% from the expected value, a re-computation is triggered. Alternatively, the re-computation limit may be based on the expected deviation from the session target. For example, if only 80% of the intended mass of urea is expected to be removed, a re-computation is triggered. In yet an alternative, the re-computation limit may be based on the expected deviation from the therapeutic targets. For example, if the plasma sodium concentration after treatment is predicted to exceed the therapeutic target by more than 3 mmol/L, a re-computation is triggered.

It is conceivable that the user is allowed to modify the suggested control settings such that the dialysis machine is unable to reach the targets. Suitably, the system requests the user to acknowledge that the targets will not be reached, and then the treatment may begin/continue anyway. The treatment "debt" that is left will automatically be corrected in the next treatment session, since the patient status then will indicate a need for more dialysis.

All of the above-described methods, processes and steps may be implemented by the logic device 11 shown in FIG. 1. All or part of the functionality of the logic device 11 may be provided by dedicated hardware and/or by special-purpose software (or firmware) run on one or more general-purpose or special-purpose computing devices. In this context, it is to be understood that each "element" or "means" of such a computing device refers to a conceptual equivalent of a method step; there is not always a one-to-one correspondence between elements/means and particular pieces of hardware or software routines. One piece of hardware sometimes comprises different means/elements. For example, a processing unit serves as one element/means when executing one instruction, but serves as another element/means when executing another instruction. In addition, one element/means may be implemented by one instruction in some cases, but by a plurality of instructions in some other cases. Such a software-controlled computing device may include one or more processing units, e.g. a CPU ("Central Processing Unit"), a DSP ("Digital Signal Processor"), an ASIC ("Application-Specific Integrated Circuit"), discrete analog and/or digital components, or some other programmable logical device, such as an FPGA ("Field Programmable Gate Array"). The computing device may further include a system memory and a system bus that couples various system components including the system memory to the processing unit. The system bus may be any of several types of bus structures including a memory bus or memory controller, a peripheral bus, and a local bus using any of a variety of bus architectures. The system memory may include computer storage media in the form of volatile and/or non-volatile memory such as read only memory (ROM), random access memory (RAM) and flash memory. The special-purpose software may be stored in the system memory, or on other removable/non-removable volatile/non-volatile computer storage media which is included in or accessible to the computing device, such as magnetic media, optical media, flash memory cards, digital tape, solid state RAM, solid state ROM, etc. The special-purpose software may be provided to the computing device on any suitable computer-readable medium, including a record medium, a read-only memory, or an electrical carrier signal. It is also conceivable that certain signal processing is fully or partially implemented by dedicated hardware, such as an FPGA, an ASIC, or an assembly of discrete electronic components (resistors, capacitors, operational amplifier, transistors, filters, etc), as is well-known in the art.

As a further illustration, FIG. 5 is a block diagram of a logic device 11 that provides the control settings in the method of FIG. 2. The logic device 11 comprises means 51A-56 which directly correspond to the steps 21A-26 described above with reference to FIG. 2. Thus, the logic device comprises means 51A for determining the current status, means 51B for obtaining the therapeutic targets, means 52 for computing the control settings, means 53 for presenting the control settings, means 54 for detecting an operator-initiated modification of the control settings, means 55 for making the control settings available to the dialysis machine for performing the treatment session, and means 56 for detecting a change in any relevant parameter during the treatment session.

The invention has mainly been described above with reference to a few embodiments. However, as is readily appreciated by a person skilled in the art, other embodiments than the ones disclosed above are equally possible within the scope and spirit of the invention, which is defined and limited only by the appended patent claims.

For example, the dialysis system may be controlled to achieve only one or a few physiological targets. In one example, the control settings are computed to achieve only dry weight and a (maximum) plasma concentration of urea after the treatment session. In this case, the settings for electrolytes (e.g. Na, K, Ca, $HCO_3$) are fixed according to the physician's prescription. This means that the task of determining the pre-dialysis patient status is considerably simplified.

It is also to be understood that there are many alternative or supplementary therapeutic targets, and that the examples of physiological targets given herein may be formulated differently. For example, physiological targets for removal or uremic toxins may comprise a plasma concentration of creatinine, vitamin B12, or β-2-microglobuline. Physiological targets for fluid balance may comprise the blood pressure (systolic or diastolic) of the patient. Further physiological targets may comprise the body temperature of the patient, since it may be desired to lower the body temperature during the treatment session to reduce the likelihood of treatment-induced hypotension, Yet further physiological targets may comprise hematocrit or hemoglobin concentration. If such alternative or supplementary physiological targets are used, then clearly also other measures of the patient status will be used.

It is also to be noted that session targets need not be used. For example, Eq. 9-13 may be re-formulated to provide functional relations between the target value of each physiological parameter and the pre-dialysis value of the physiological parameter.

It should also be understood that the inventive concept is applicable to other types of renal replacement therapy, including but not limited to hemofiltration (HF), hemodiafiltration (HDF), peritoneal dialysis (PD), and pure ultrafiltration (UF). In these cases, the control settings (machine-related parameters) may be different and anyone skilled in the art may easily find suitable control settings.

The invention claimed is:

1. A dialysis system comprising:
a dialysis machine configured to perform treatment sessions of renal replacement therapy, and
a logic device for generating control settings of machine-related parameters of the dialysis machine,
wherein the dialysis machine is configured to obtain from the logic device, prior to each treatment session for an individual patient, a set of current control settings of the machine-related parameters to be applied in the treatment session, and wherein the logic device is configured to:
obtain a set of therapeutic targets comprising a target value of one or more physiological parameters for the patient, wherein the target value represents part of a desired status of the patient after the treatment session, and wherein the set of therapeutic targets includes a target value of (i) a measure of a property of the patient's blood including at least one of urea concentration, an electrolyte concentration, and an acid-base balance and (ii) a measure of a fluid balance of the patient;
obtain status data that represents a current status of the patient prior to the treatment session; and
compute, as a function of the set of therapeutic targets and the status data, the set of current control settings of the machine-related parameters, wherein the logic device is configured to compute at least part of the current control settings based on a predictive model that estimates the physiological response of the patient to the machine-related parameters during the treatment session, such that the set of current control settings of the machine-related parameters enable the dialysis machine to achieve said target value of one or more physiological parameters including the target value of (i) a measure of a property of the patient's blood including at least one of a urea concentration, an electrolyte concentration, and an acid-base balance and (ii) a measure of a fluid balance of the patient at the end of the treatment session.

2. The dialysis system of claim 1, wherein the set of therapeutic targets represents the desired status of the patient after the treatment session.

3. The dialysis system of claim 1, wherein the status data comprises a starting value of said one or more physiological parameters before the treatment session.

4. The dialysis system of claim 3, wherein the logic device is configured to estimate the starting value of said one or more physiological parameters based on historic data for the patient.

5. The dialysis system of claim 4, wherein the historic data indicates a rate of change for at least one physiological parameter.

6. The dialysis system of claim 4, wherein the historic data comprises data related to one or more preceding treatment sessions, including at least one of a time between treatment sessions, a duration of one or more preceding treatment sessions, a clearance obtained in one or more preceding treatment sessions, a final value of said one or more physiological parameters in one or more preceding treatment sessions.

7. The dialysis system of claim 4, wherein the logic device is configured to estimate the starting value of said one or more physiological parameters by means of a further predictive model that estimates the status of the patient based on the historic data.

8. The dialysis system of claim 3, wherein the logic device is configured to calculate session targets as a difference between the target and starting values for each physiological parameter, and compute the current control settings as a function of the session targets.

9. The dialysis system of claim 1, wherein the logic device is configured to compute said at least part of the current control settings by finding one solution to a set of functional relations, wherein each functional relation is based on the predictive model and links one of said one or more physiological parameters to one or more machine-related parameters.

10. The dialysis system of claim 9, wherein the logic device is configured to find said one solution by computing the values of the machine-related parameters according to a predetermined priority order.

11. The dialysis system of claim 10, wherein the logic device is further configured to obtain a data structure that defines the predetermined priority order.

12. The dialysis system of claim 9, wherein the logic device is configured to find said one solution by computing the values of the machine-related parameters based on predetermined value definitions for the values of the machine-related parameters.

13. The dialysis system of claim 12, wherein the logic device is further configured to obtain a data structure that contains the value definitions.

14. The dialysis system of claim 12, wherein the value definitions comprise at least one of:
setting the value of at least one machine-related parameter to a predetermined value,
setting the value of at least one machine-related parameter to a minimum,
setting the value of at least one machine-related parameter to a maximum, and
setting the value of at least one machine-related parameter to any value.

15. The dialysis system of claim 12, wherein the value definitions indicate a dialysis fluid flow rate to be set to achieve saturation, and wherein the priority order prioritizes the dialysis fluid flow rate over a duration of the treatment session.

16. The dialysis system of claim 12, wherein the value definitions indicate a given amount of dialysis fluid to be utilized over the duration of the treatment session, and wherein the priority order prioritizes the amount of dialysis fluid and the duration of the treatment session over the dialysis fluid flow rate.

17. The dialysis system of claim 12, wherein the value definitions indicate the duration of the treatment session to be set to a minimum, and wherein the priority order prioritizes the duration of the treatment session over other machine-related parameters.

18. The dialysis system of claim 1, wherein the logic device is configured to set the duration of the treatment session to a predetermined value when computing the current control settings.

19. The dialysis system of claim 1, wherein the logic device configured to separately compute a minimum duration of the treatment session to reach the target value for each physiological parameter, and set a duration of the treatment session to the maximum of the minimum durations, wherein the logic device is configured to compute the current control settings based on the thus-set duration.

20. The dialysis system of claim 1, wherein the logic device is configured to compute the current control settings for the machine-related parameters without user intervention.

21. The dialysis system of claim 1, wherein the dialysis machine is configured to perform the treatment session using the current control settings.

22. The dialysis system of claim 21, which is configured to, before the dialysis machine performs the treatment session, present at least part of the current control settings for approval by a user.

23. The dialysis system of claim 22, which is configured to, if a modification of one or more current control settings is received after presenting said at least part of the current control settings, cause the logic device to compute updated control settings based on the modification.

24. The dialysis system of claim 1, which is configured to, if detecting a deviating value of a physiological or machine-related parameter during the treatment session, cause the logic device to compute updated control settings based on the deviating value.

25. The dialysis system of claim 1, wherein the machine-related parameters comprise at least one of a duration of the treatment session, a dialyzer type, a blood flow rate, a dialysis fluid flow rate, a dialysis fluid composition, and an ultrafiltration rate.

26. The dialysis system of claim 1, wherein the dialysis machine is configured for one of hemodialysis, hemodiafiltration, hemofiltration and peritoneal dialysis.

27. Use of the dialysis system as defined in claim 1 for performing a treatment session on a patient.

28. Use of the dialysis system as defined in claim 1 for performing one of hemodialysis, hemodiafiltration, hemofiltration and peritoneal dialysis.

29. A logic device for generating control settings to a dialysis machine which is configured to perform treatment sessions of renal replacement therapy, said logic device being adapted to generate, prior to each treatment session for an individual patient, a set of current control settings of machine-related parameters to be applied in the treatment session, said logic device comprising:
   means for obtaining a set of therapeutic targets comprising a target value of one or more physiological parameters for the patient, wherein the target value represents part of a desired status of the patient after the treatment session and wherein the set of therapeutic targets includes a target value of (i) a measure of a property of the patient's blood including at least one of urea concentration, an electrolyte concentration, and an acid-base balance and (ii) a measure of a fluid balance of the patient;
   means for obtaining status data that represents a current status of the patient prior to the treatment session; and
   means for computing, as a function of the set of therapeutic targets and the status data, the set of current control settings of the machine parameters, wherein the means for computing is configured to compute at least part of the current control settings based on a predictive model that estimates the physiological response of the patient to the machine-related parameters during the treatment session, such that the set of current control settings of the machine-related parameters enable the dialysis machine to achieve said target value of one or more physiological parameters including the target value of (i) a measure of a property of the patient's blood including at least one of a urea concentration, an electrolyte concentration, and an acid-base balance and (ii) a measure of a fluid balance of the patient at the end of the treatment session.

30. A method of obtaining control settings for a dialysis machine which is configured to perform treatment sessions of renal replacement therapy, said method comprising, prior to each treatment session for an individual patient,
   obtaining a set of therapeutic targets comprising a target value of one or more physiological parameters for the patient, wherein the target value represents part of a desired status of the patient after the treatment session, and wherein the set of therapeutic targets includes a target value of (i) a measure of a property of the patient's blood including at least one of urea concentration, an electrolyte concentration, and an acid-base balance and (ii) a measure of a fluid balance of the patient;
   obtaining status data that represents a current status of the patient prior to the treatment session; and
   computing, as a function of the set of therapeutic targets and the status data, a set of current control settings of machine-related parameters to be controlled during the treatment session, wherein at least part of the current control settings is computed based on a predictive model that estimates the physiological response of the patient to the machine-related parameters during the treatment session, such that the set of current control settings of the machine-related parameters enable the dialysis machine to achieve said target value of one or more physiological parameters including the target value of (i) a measure of a property of the patient's blood including at least one of a urea concentration, an electrolyte concentration, and an acid-base balance and (ii) a measure of a fluid balance of the patient at the end of the treatment session.

* * * * *